United States Patent [19]

Carter et al.

[11] Patent Number: 4,814,160

[45] Date of Patent: Mar. 21, 1989

[54] NON-BLEEDING STRIPED DENTIFRICE

[75] Inventors: Willie J. Carter, Belle Mead; Denise D. Suttmeier, Somerville, both of N.J.

[73] Assignee: Colgate-Palmolive Company, New York, N.Y.

[21] Appl. No.: 162,767

[22] Filed: Mar. 1, 1988

[51] Int. Cl.$^4$ .................. A61K 7/16; A61K 7/18; A61K 7/26

[52] U.S. Cl. .................. 424/7.1; 424/49; 424/52; 424/57; 424/58

[58] Field of Search .................. 424/7.1, 49–58

[56] References Cited

U.S. PATENT DOCUMENTS

| | | | |
|---|---|---|---|
| 3,928,559 | 12/1975 | Patino | 424/49 |
| 3,980,767 | 9/1976 | Chown | 424/52 |
| 4,007,259 | 2/1977 | Patino | 424/49 |
| 4,069,311 | 1/1978 | Mannara | 424/49 |
| 4,069,312 | 1/1978 | Mannara | 424/49 |
| 4,202,878 | 5/1980 | Ritze et al. | 424/7.1 |
| 4,358,437 | 11/1982 | Duke | 424/52 |
| 4,376,762 | 3/1983 | Hauschild et al. | 424/7.1 |
| 4,376,763 | 3/1983 | Barth et al. | 424/7.1 |
| 4,440,877 | 4/1984 | Hauschild et al. | 424/7.1 |
| 4,444,746 | 4/1984 | Harvey et al. | 424/7.1 |
| 4,456,585 | 6/1984 | Hayes et al. | 424/7.1 |
| 4,487,757 | 12/1984 | Kiozpeoplou | 424/7.1 |
| 4,518,578 | 5/1985 | Hayes et al. | 424/7.1 |
| 4,568,534 | 2/1986 | Stier | 424/7.1 |

*Primary Examiner*—Shep K. Rose
*Attorney, Agent, or Firm*—Murray M. Grill; Robert L. Stone

[57] ABSTRACT

A stable two component striped dentifrice wherein there is no bleeding of the coloring material from the striped component into the white base component, said components having different formulations.

18 Claims, No Drawings

NON-BLEEDING STRIPED DENTIFRICE

BACKGROUND OF THE INVENTION AND PRIOR ART

A major problem encountered in the production of a two component striped toothpaste is the bleeding of color from one component into the other. This is essentially severe if the colored component is applied to the surface of a white base. In this case the concentration of colorant added to the striping component has to be very high in order to compensate for the thinness of the stripe. If any bleeding is present it is quite noticeable. For this reason a colorant that exhibits no bleeding is required.

Striped dentifrice products containing water soluble dyes are known in the prior art as disclosed in U.S. Pat. No. 4,358,437, U.S. Pat. No. 4,568,534 and U.S. Pat. No. 4,487,757. U.S. Pat. No. 4,358,437 discloses a striped toothpaste wherein the water soluble dye is in a clear gel phase with an opaque paste stripe containing the calcium carbonate abrasive and the metasilicate ingredient within or on the transparent gel containing monofluorophosphate. U.S. Pat. No. 4,568,534 discloses a stripe dentifrice comprising a white anhydrous toothpaste formulation and an aqueous striping composition containing a pH sensitive dye and a gelling agent mixture of carboxymethyl cellulose and calcium carrageenan. U.S. Pat. No. 4,487,757 discloses an effervescent toothpaste extruded from a tube comprising two separate portions, one portion containing sodium bicarbonate particles, stabilized by a compatible water insoluble polishing agent such as calcium carbonate, and a second portion having an acid pH and containing an acid and preferably 0.001 to 0.1% of a coloring agent which is a 1% aqueous dye solution.

However, previous testing has shown that water soluble dyes bleed in our normal stripe formulations. Pigments do not exhibit bleeding. Accordingly, synthetic pigments such as phthalocyanine have been used in a colored dentifrice stripe as disclosed in U.S. Pat. No. 4,456,585 and U.S. Pat. No. 4,518,578. However, said synthetic phthalocyanine pigments are disallowed for use in dentifrices in many countries around the world. Therefore, alternate non-bleeding colorant and/or formulation is needed.

It has been found that naturally occurring organic pigments such as chlorophyllin (green) and B-carbonate (yellow) as colorants showed no bleeding when combined with high levels of xanthan gum (at least 1.6%) in the colored phase of a striped dentifrice.

The prior art also discloses speckled dentifrices wherein the speckles contain a colorant blended with the water-insoluble thermoplastic polymer paricles such as polyethylene, said colorant being a pigment such as ultramarine blue, ferric oxide, metallic lakes and the like, as disclosed in U.S. Pat. No. 3,928,559 and U.S. Pat. No. 4,007,259. U.S. Pat. No. 4,007,259 has addressed the bleeding of colorant from the colored speckle into the toothpaste base by adding 1-5% chloroform to the dental cream, or by adding carnauba wax or a polishing agent to the colored speckles to provide color stability and bleed resistance. U.S. Pat. No. 4,069,311 and U.S. Pat. No. 4,069,312 also disclose speckled dentifrices, wherein said speckles are thermoplastic binder material containing colorants including any physiologically acceptable dye or pigment such as inorganic pigments, organic dyes, metallic lakes thereof, chlorophyll and carotene.

U.S. Pat. No. 3,980,767 discloses a toothpaste consisting of a main transparent gel body free of dental abrasive and containing humectant, thickening agent such as cellulose esters or carrageenates; and a secondary gel body containing a dental abrasive, humectants, thickening agents, detergent and optionally an insoluble coloring material in the form of a contrasting stripe within the main gel body.

However, there is no disclosure in the prior art of a non-bleeding striped dentifrice comprising a white paste dental component and a colored gel dental component having different formulae; said colored component containing the organic pigments beta-carotene or chlorophyllin in a translucent high water gel containing a xanthan gum gelling agent, a sorbitol humectant system and an abrasive polishing agent; said white base component containing the cellulase resistant gelling agent Viscarin (a kappa carrageenan mixture) in an aqueous paste containing glycerin or a mixed humectant system, a polishing agent and other conventional dental ingredients such as anionic surfactant, fluoride-containing compounds, flavors, and the like.

SUMMARY OF THE INVENTION

It has now been found that a two component stable striped dentifrice can be formulated that does not exhibit bleeding from one component into the other component. In order to decrease the transport of colorant at the interface from one component to the other, the two component dentifrices have quite different formulae. One component consists of the coloring agent in a translucent high water gel, while the white component is an opaque white paste. The gelling agent used in the pigmented gel component is Xanthan gum at high concentrations to further decrease bleeding. Because this gum always has a small amount of cellulase present, the gelling agent used in the white paste component has to be cellulose resistant. Accordingly, the gelling agent used in the white paste is Viscarin, a kappa carrageenan mixture which is cellulase resistant. Two coloring agents were found to exhibit no bleeding in this system, i.e. beta-carotene (yellow) and chlorophyllin (green). The high water gel component comprises a humectant system containing a major amount of sorbitol and/or maltitol, and a dentally acceptable polishing agent, preferably a silica polishing agent. The white paste component comprises a humectant system containing a major amount of glycerin, and dicalcium phosphate dihydrate polishing agent. An advantage of this invention over the prior art is that it allows for the manufacture of a two component, two color dentifrice in which one color does not bleed into the other.

Accordingly, it is a primary object of the instant invention to provide a stable, non-bleeding striped dentifrice comprising two components having different formulations, a clear or translucent high water gel dentifrice containing an organic pigment selected from the group consisting of B-carotene and chlorophyllin, and a white paste dentifrice.

Another object of the invention is to provide a stable non-bleeding two-component stripe formulation wherein the pigmented gel component contains high concentrations of xanthan gum as the sole gelling agent.

Still another object of the invention is to provide a stable two component non-bleeding striped dentifrice wherein the white paste component contains a cellulase resistant gelling agent such as a kappa carrageenan mixture, particularly Viscarin.

Additional objects, advantages and novel features of the invention will be set forth in part in the description which follows, and in part will become apparent to those skilled in the art upon examination of the following specification or may be learned by practice of this invention.

To achieve the foregoing and other objects in accordance with the present invention, as embodied and broadly described herein, the stable, non-bleeding striped dentifrice compositions of this invention consists essentially of a combination of two dentifrice components having different formulations, a clear or translucent high water gel colored dentifrice component comprising an organic pigment selected from the group consisting of B-carotene and chlorophyllin, and xanthan gum as the sole gelling agent; and a white paste dentifrice component comprising a cellulase resistant gelling agent, i.e. a kappa carrageenan mixture, in a distinctly different liquid vehicle containing different dentally acceptable polishing agents.

More specifically, present invention relates to a stable non-bleeding striped dentifrice composition consisting essentially of a combination of two dentifrice components, a clear or translucent high water gel colored dentifrice component and a white paste base dentifrice component having different formulations to prevent the migration of the color at the interface of the two dentifrice components; said gel component comprising about 0.01–0.5% by weight of an organic pigment selected from the group consisting of B-carotene and chlorophyllin, and at least 1.6% xanthan gum as the sole gelling agent, in a liquid vehicle comprising about 35–40% total water and about 30–40% by weight of a humectant system containing a major amount of sorbitol or maltitol and mixtures thereof and optionally minor amounts of glycerin, polyethylene glycol 600 and/or propylene glycol, and a dentally acceptable polishing agent, preferably a silica polishing agent; said white paste component comprising a cellulase resistant gelling agent selected from a kappa carrageenan mixture, particularly a mixture of lambda- and kappa carrageenans, in a liquid vehicle comprising about 20–25% water and about 20–25% by weight of a humectant system containing a major amount of glycerin and optionally minor amounts of sorbitol, maltitol, polyethylene glycol 600 and/or propylene glycol, and a dicalcium phosphate dihydrate polishing agent.

DETAILED DESCRIPTION OF THE INVENTION

In accordance with this invention, the clear or translucent gel dentifrice component contains minor amounts of an oil soluble, natural organic pigment including beta-carotene which is yellow and chlorophyllin which is green as the coloring material. These pigments do not exhibit color bleeding into an adjacent white or color-free dentifrice composition. B-carotene is a plant pigment having a melting point of 184° C. Chlorophyllin is the chromoprotein green coloring matter of plants, a soft green mass insoluble in water, from colloidal solutions in organic solvents, marketed as copper or zinc compounds. The pigment constitutes about 0.01–0.5% by weight of the gel component and preferably about 0.01–0.1%.

Another essential ingredient in the clear or translucent colored gel dentifrice component is the presence of high concentrations of at least 1.6 up to 3.0% by weight of xanthan gum as the sole gelling agent, which further decreases bleeding of the coloring material. Xanthan gum is a fermentation product prepared by action of the bacteria of the genus Xanthomonas upon carbohydrates. Four species of Xanthomonas, viz *X campetris, X phaseoli, X malvocearum* and *X carotae* are reported in the literature to be the most efficient gum producers. Although the exact chemical structure is not determined, it is generally accepted to be a heteropolysaccharide with a molecular weight of several million. It contains D-glucose, D-mannose and D-glucuronic acid in the molar ratio of 2.8:3.0:2.0. The molecule contains 4.7% acetyl and about 3% pyruvate. The proposed chemical structure configuration can be found in McNeely and Kang, Industrial Gums, ed. R. L. Wistler, CH XXI, 2nd Edition, New York, 1973. The procedure for growing, isolating and purifying the xanthan gum is also found in that publication. Further description of xanthan gum is found in Manufacturing Chemist, May 1960, pages 206–208 (including mention at page 208 of potential use of gums therein described for formulating toothpastes).

The gelling agent in the white paste dentifrice component must be a cellulase resistant gelling agent because the xanthan gum in the colored gel dentifrice always contains a small amount of cellulase. Accordingly, a kappa-carrageenan mixture, which is cellulase resistant is used in the white paste dentifrice as the sole gelling agent. The kappa-carrageenan mixture may contain mixtures of sodium salts of lambda and kappa-carrageenans; calcium, potassium and sodium salts of lambda, kappa and iota carrageenans, and the like. The molecular weight of the carrageenans will normally be in the range of 5,000 to about 500,000, with most of those commercially employed being in the range of about 100,000 to 500,000. Preferably, such molecular weights will be in the range of 225,000 to 275,000. The gel-sol transition temperatures for the carrageenans vary depending on the particular carrageenan or carrageenan mixture and the compositions of the medium in which it is present. Thus, for 1% of kappa-carrageenan in water, the gelling temperature can be raised from about 5° C. to as high as 60° C. by increasing the potassium ion content from 0 to about 1%. Similarly, with respect to iota-carrageenan, an increase in the calcium ion content from 0 to 1% may increase the gelling temperature from about 44° C. to 72° C. The gelling of kappa-carrageenan is usually effected by heating to a temperature of about 70° C., or more, followed by cooling, with a firm gel usually being formed at a temperature between 45° and 65° C., which remelts when the temperature is raised 10° to 20° C. above the setting temperature. When lambda-carrageenan is mixed with kappa-carrageenan, as in the preferred gelling agents of the present invention, it has been found that in the dentifrice compositions described, the gel-sol point may be in the range of 45° to 49° C. If, technically, this temperature does not result in gel-sol transition, nevertheless, an improvement in viscosity or thickness of the product is obtained by heating it to such a temperature, or higher. A preferred carrageenan mixture is that sold under the name Viscarin R GMC. The amount of the carrageenan mixture in the white paste dentifrice component is about 0.1 to 3% by weight.

The two dentifrice components of present invention contain liquid vehicles comprising humectant and water. The clear or translucent pigmented gel dentifrice component comprises about 30–40% by weight of a humectant system containing a major amount of sorbitol, maltitol and mixtures thereof and optionally minor amounts of about 0–5% glycerin, and a high water content of about 35–40% total water by weight. The liquid vehicle of the gel dentifrice typically comprises abut 65–75% by weight of the gel. The white paste dentifrice component comprises lesser amounts of humectant and water, more specifically, about 20–25% by weight of a humectant system containing a major amount of glycerin and optionally minor amounts of about 0–7% sorbitol or maltitol, and about 20–25% total water by weight. Other humectants such as polyethylene glycol 600 and propylene glycol may partially replace the sorbitol and/or the glycerine humectant. The liquid vehicle of the paste dentifrice typically comprises about 40–50% by weight of the paste.

The paste dentifrice component of present two component, two color dentifrice contains about 45–50% dicalcium phosphate dihydrate as the water insoluble dental polishing agent; and the pigmented translucent gel component contains a different dentally acceptable polishing agent in an amount of about 20–25% by weight of the gel composition. Representative polishing agents include for example, calcined alumina, calcium carbonate, hydrated alumina, silica (which includes sodium aluminosilicate and/or silica containing combined alumina), zirconium silicate and the like.

The average particle size of the calcium carbonate is preferably between less than 20 microns and 1 micron, and preferably below 10 microns and about 1 micron. The silica may be of crystalline or amorphous type. In either case the particle size is preferably below 20 microns, e.g., 2 to 10 microns. Micronized crystalline silica or silica gel, such as the silica gel sold under the trade name Syloid 63, Syloid 74, and the like, are examples of useful silicas. The alumina may be of the hydrated or unhydrated type. For hydrated alumina the average particle size is preferably between less than 20 microns and 1 micron, most preferably below 10 microns and about 1 or 2 microns. When zirconium silicate is employed its average particle size is preferably between less than 5 microns to 0.3 micron, e.g., below 3 microns and about 0.3 micron.

A particularly suitable alumina is in the form of flat flakes of alpha-alumina crystals, or disk- or plate-like configuration. Said flakes have a mean (by weight) particle demeter of less than about 7 microns, e.g. about 2 to 7 microns. The flat alpha-alumina crystals and a process for preparing them are described in U.S. Pat. No. 3,121,623. While it is most preferred to use alumina flakes, the mean particle diameter of which is less than five microns, e.g., about 3 to 4 microns, it is within the broader scope of this invention to use alumina flakes of larger diameters but similar thickness, such as alumina flakes that are described in the aforesaid U.S. Pat. No. 3,121,623 having average diameters of 9, 12 or 15 or more microns, free of particles over 40 microns in diameter (preferably free of particles over about 20 microns in diameter), and substantially free of particles having a thickness above about 3 microns. It is also within the broader scope of the invention to include other alpha-aluminas or other polishing agents of suitable hardness, sometimes about 6 on the Moh scale, in admixture with the alpha-alumina flakes. For instance, one may replace about one-half of the alumina flakes with a pulverized alpha-alumina of irregular shape and having a resin particle size of about 3 to 4 microns (with all said irregular particles being less than about 7 microns in their largest dimension).

A typical alkali or alkaline earth metal aluminosilicate is a complex having a refractive index of about 1.45, a moisture content of about 5 to 20%, e.g. 10%, an alumina content of up to about 10%, e.g. 8%, a silica content of at least about 70%, a sodium oxide (or other alkali metal or alkaline earth metal oxide, e.g. calcium oxide) content of up to about 10%, e.g. 7%, and a particle size of below 40 microns, preferably about 1 to 20 microns. The preferred polishing agent is a silica dental polishing agent.

In accordance with this invention, the pigmented clear or translucent gel dentifrice component is combined with the non-colored or white paste dentifrice component, said pigmented gel forming a colored stripe(s) on the surface of the paste dentifrice or within the body of the paste dentifrice. Likewise, the white paste component may form a white stripe(s) on the surface of the pigmented gel dentifrice or within the body of the pigmented gel dentifrice. The proportion of surface striped component to the base component is preferably in the ratio of about 10:90 or 12:88 percent by weight. In the deep striped dentifrices, the proportion of the white paste dentifrice to the pigmented gel dentifrice is in the ratio of 60:40% or 40:60% by weight. In these striped dentifrices, the striped dentifrice component and the base dentifrice component are of different formulations in order to prevent the transport of the color at the interface from one component to the other.

In vitro tests for color bleeding were performed on 2-component dentifrice compositions containing the same ingredients except for the presence of a colorant in one component only. Two ounce jars were ¼ way filled with the white base paste, then the green paste containing 0.5% of a 1% solution of D&C Green #5 (a dye) was placed on the white paste. A red line was drawn around the jar where the white met the green and the jars were placed in a 120° oven for a night. The formulation of the white paste is set forth in Example 1, hereinafter defined. The green formula bled into the white paste overnite. A combination of D&C Yellow #10 and FD and C blue #1 was substituted for the D&C Green #5 which also failed in the color bleeding test. The substitution of a D&C Blue #1 dye also failed the color bleeding test. The formula for the colored dentifrice was changed to the gel formulation of Example 1 except that the colorant was combination of the yellow and blue dyes. This composition also failed for color bleeding. Omitting the flavor from the green formula also failed for color bleeding. Dry beta carotene was added to the FD&C Blue #1 dye in the gel formula and tested for color bleeding. Only the blue color ran, not a green color. The beta carotene did not bleed. Substituting a FDC Blue #1 lake for the FDC blue dye gave the same results. The blue is the only color to bleed. Chlorophyllin was substituted for the combination of blue dye and the beta-carotene which resulted in a non-bleeding green formula when tested in vitro. These tests clearly show the specificity of colorant and the need for different formulations in a two-component striped dentifrice.

The two component dentifrice may also contain surface-active agents, e.g., to achieve increased prophylactic action, assist in achieving thorough and complete dispersion of the instant compositions throughout the oral cavity, and render the instant compositions more cosmetically acceptable. The organic surface-active material may be anionic, nonionic, amphoteric, or cationic in nature, and it is preferred to employ as the surface active agent a detersive material which imparts to the composition detersive and foaming properties. Suitable types of such detergents are water soluble salts of higher fatty acid monoglyceride monosulfates, such as sodium salt of the monosulfonated monoglyceride or hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher acid ester of 1,2-hydroxypropane sulfonates, and the substantially saturated higher aliphatic acyl amides of lower aliphatic amino carboxylic acid compounds, such as those having 12 to 16 carbons in the fatty acid alkyl or acyl radicals, and the like. Examples of the last-mentioned amides are N-lauroyl sarcosine and the sodium, potassium, and ethanolamine salts of N-lauroyl, N-myristoyl or N-palmitoyl sarcosinates, which should be substantially free from soap or similar higher fatty acid material which tends to substantially reduce the effect of these compounds. The use of these sarcosinate compounds in dentifrice compositions of the present invention is particularly advantageous since these materials exhibit a prolonged and marked effect in the inhibition of acid in the oral cavity due to carbohydrates, in addition to exerting some reduction in the solubility of tooth enamel in acid solutions.

Other suitable surface active materials include non-ionic agents such as condensates of sorbitan monostearate with approximately 60 moles of ethylene oxide, condensates of ethylene oxide with propylene oxide condensates of propylene glycol ("Pluronics"), and cationic surface active germicides and antibacterial compounds such as di-isobutylphenoxyethyldimethyl benzyl ammonium chloride, benzyl dimethyl stearyl ammonium chloride, tertiary amines having one fatty alkyl group (of from 12 to 18 carbon atoms) and two (poly) oxyethylene groups attached to the nitrogen (typically containing a total of from about 2 to 50 ethenoxy groups per mole) and salts thereof with acids, and compounds of the structure:

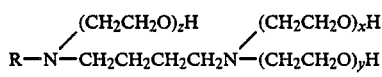

where R is a fatty alkyl group containing from about 12 to 18 carbon atoms, and x, y and z total 3 or higher, as well as salts thereof with mineral organic acids, may also be used. It is preferred that the total amount of surface-active agent be about 0.05–5% by weight, preferably about 1–3% in each of the two dentifrice components of the two component striped dentifrice or in one of the components.

The compositions of the present invention, may also contain a fluoride-containing compound having a beneficial effect on the care and hygiene of the oral cavity, e.g. diminution of enamel solubility in acid and protection of the teeth against decay. Examples thereof include sodium fluoride, stannous fluoride, potassium fluoride, potassium stannous fluoride ($SNF_2$-KF), potassium fluorozirconate, sodium hexafluorostannate, stannous chlorfluoride, and sodium monofluorophosphate. These materials, which dissociate or release fluorine-containing ions, suitably may be present in an effective but non-toxic amount, usually within the range of about 0.1 to 2% by weight in the white paste component and preferably also in the colored stripe gel component based on the water soluble fluorine content thereof. Sodium fluoride, stannous fluoride and sodium monofluorophosphate are particularly preferred, as well as mixtures thereof.

Various other materials may be incorporated in the oral preparation of this invention. Examples thereof are whitening agents such as titanium dioxide, preservatives such as sodium benzoate, anticorrosive agents such as dicalcium phosphate dihydrate, antiplaque and antibacterial agents, flavors and sweeteners such as sodium saccharin, and other constituents. Each of these adjuvants may be typically incorporated in the instant toothpastes in amounts up to 5% provided they do not adversely affect the stability and cleaning properties of the non-bleeding striped dentifrice of present invention.

Each of the dentifrice components is typically prepared separately, in a state of the art vacuum mixing apparatus by blending the gelling agent with a portion of the liquid vehicle including water and humectant, to form a dispersion. Then the remaining liquid is separately blended with the polishing agent and additional components such as surfactant, pigment, etc. to form another dispersion. Then the two dispersion are blended together, followed by the addition of saccharin, flavor and the monofluorophosphate, each separately predissolved in water, and mixing until a homogeneous dentifrice component (a gel or paste) is formed. The apparatus can be used to blend ingredients at room temperature as well as at higher temperatures.

The striped dentifrice is obtained by combining the gel and paste components using a tube filling machine. The dentifrice should have a pH practicable for use e.g. a slightly acid to slightly alkaline pH is preferred. The striped dentifrice may be packaged in the tubes or dispensers adapted therefor.

The following examples are given to illustrate this invention further, but it is understood that the invention is not limited thereto. Dentifrice formulations are prepared in the usual manner except as indicated, and all amounts and proportions are by weight except as otherwise indicated.

EXAMPLE 1

A yellow striped toothpaste having the following formulations was prepared:

| WHITE BASE PASTE FORMULATION | |
|---|---|
| Ingredients | % |
| Glycerine | 22.00 |
| Viscarin[1] | 1.10 |
| Tetrasodium Pyrophosphate | 0.50 |
| Sodium Saccharin | 0.20 |
| Sodium Monofluorophosphate | 0.76 |
| Deionized Water | 24.24 |
| Dicalcium Phosphate Dihydrate | 48.00 |
| Flavour | 1.20 |
| Sodium Lauryl Sulphate | 2.00 |
| | 100.00 |

[1] A mixture of kappa carrageenan and lambda carrageenan

| YELLOW STRIPE GEL FORMULATION | |
|---|---|
| Ingredient | % |
| Glycerine | 5.00 |
| Xanthan Gum | 1.60 |
| Sorbitol (70% soln.) | 43.00 |
| Sodium Saccharin | 0.20 |
| Sodium Monofluorophosphate | 0.76 |
| Deionized Water | 24.20 |

-continued

YELLOW STRIPE GEL FORMULATION

| Ingredient | % |
|---|---|
| Zeo 49 (Silica)[1] | 22.00 |
| Dicalciumphosphate Dihydrate | 0.20 |
| Flavour | 1.20 |
| Sodium Lauryl Sulphate | 1.80 |
| B-Carotene (2.4% Beadletts)[2] | 0.04 |

[1]Silica containing low combined alumina (circa 1%); J. M. Huber Corp.
[2]Hoffman-La Roche, Inc.

The white paste dentifrice is combined with the yellow gel dentifrice in a tube filling machine in the formation of a non-bleeding yellow striped dentifrice upon extrusion, said striped dentifrice comprising 10% of the yellow gel dentifrice and 90% of the white paste dentifrice.

This two component striped dentifrice is stable and does not exhibit bleeding from the yellow colored stripe component into the white base component.

EXAMPLE 2

A green striped toothpaste having the White Base Paste Formulation of Example 1 and the following green stripe gel formulation was prepared:

GREEN STRIPE GEL FORMULATION

| Ingredient | % |
|---|---|
| Glycerine | 5.00 |
| Xanthan Gum | 1.60 |
| Sorbitol (70% Soln.) | 43.00 |
| Sodium Saccharin | 0.20 |
| Sodium Monofluorophosphate | 0.76 |
| Deionized Water | 24.16 |
| Zeo 49 (Silica)[1] | 22.00 |
| Dicalciumphosphate Dihydrate | 0.20 |
| Flavour | 1.20 |
| Sodium Lauryl Sulfate | 1.80 |
| Chlorophyllin | 0.08 |

[1]Low Combined Alumina Silica; J. M. Huber Corp. A stable non-bleeding green striped dentifrice is formed.

EXAMPLE 3

The white paste Formulation of Example 1 is changed by substituting a humectant system consisting of 17% glycerine and 10% sorbitol (70% soln.) for the 22% glycerin, and the water content is adjusted accordingly. A combination of 88% of the white paste dentifrice and 12% of the yellow gel dentifrice of Example 1 produces a stable non-bleeding yellow striped dentifrice.

EXAMPLE 4

The white paste formulation of Example 3 is combined with the green gel dentifrice of Example 2 to produce a stable non-bleeding green striped dentifrice.

EXAMPLE 5

The yellow stripe gel formulation is changed by omitting the 5% glycerin ingredient and increasing the sorbitol content to 48%, and the water content is adjusted accordingly.

A combination of 10% of the yellow gel dentifrice with 90% of the white paste dentifrice of Example 1 also produces a stable, non-bleeding yellow striped dentifrice.

EXAMPLE 6

The green stripe gel formulation is changed by omitting the 5% glycerin ingredient and increasing the sorbitol content to 48%, and the water is adjusted accordingly.

A combination of 12% of the green gel dentifrice with 88% of the white paste dentifrice of Example 3 also produces a stable, non-bleeding green striped dentifrice.

The examples may be modified by substituting maltitol (70% solu.) for all or a portion of the sorbitol content in the pigmented gel formulation, without adversely affecting the non-bleeding and stability properties of the striped dentifrice.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A stable, non-bleeding striped dentifrice composition consisting essentially of a combination of two dentifrice components, a clear or translucent pigmented high water gel dentifrice component and a white paste dentifrice component having different formulations to prevent migration of the color at the interface of the two dentifrice components; said gel component comprising about 0.01–0.5% by weight of an organic pigment selected from the group consisting of B-carotene and chlorophyllin, at least 1.6% xanthan gum as the sole gelling agent, said white paste component comprising a cellulase resistant gelling agent selected from a kappa-carrageenan mixture, in distinctly different liquid vehicles containing different dentally acceptable polishing agents.

2. The composition according to claim 1, wherein the liquid vehicle of the gel dentifrice component comprises about 35–40% total water and about 30–40% by weight of a humectant system containing a major amount of sorbitol and maltitol and mixtures thereof and 0–5% glycerin.

3. The composition according to claim 1, wherein the liquid vehicle of the paste dentifrice component comprises about 20–25% water and about 20–25% by weight of a humectant system containing a major amount of glycerin and 0–7% sorbitol or maltitol.

4. The composition according to claim 1, wherein the dental polishing agent in the gel dentifrice is a silica polishing agent.

5. The composition according to claim 1, wherein the dental polishing agent in the paste dentifrice is dicalcium phosphate dihydrate.

6. The composition according to claim 1, wherein the cellulase resistant gelling agent is a mixture of kappa-carrageenan and lambda-carrageenan.

7. The composition according to claim 4, wherein the silica polishing agent constitutes about 20–25% by weight of the pigmented translucent gel dentifrice component.

8. The composition according to claim 5, wherein the dicalcium phosphate dihydrate polishing agent constitutes about 45–50% by weight of the paste dentifrice component.

9. The composition according to claim 1, wherein the proportion of the surface striped dentifrice component to the base dentifrice component is in the ratio of about 10:90% by weight.

10. The composition according to claim 1, wherein the liquid vehicle in the pigmented gel dentifrice component constitutes about 65-70% by weight, and the liquid vehicle in the paste dentifrice component constitutes about 40-50% by weight.

11. The composition according to claim 1, wherein the dental polishing agent in the gel dentifrice component constitutes about 20-25% by weight, and the polishing agent in the paste dentifrice component constitutes about 45-50% by weight.

12. The composition according to claim 1, additionally containing about 0.05-5% by weight of a surface-active agent in each of the dentifrice components or in one of the dentifrice components.

13. The composition according to claim 12, additionally containing about 0.1-2% by weight of a fluoride-containing compound in the paste dentifrice component and/or in the gel dentifrice component.

14. The composition according to claim 9 in the form of a yellow striped toothpaste containing about 0.04% by weight B-carotene coloring agent.

15. The composition according to claim 9 in the form of a green striped toothpaste containing about 0.08% by weight of chlorophyllin coloring agent.

16. The composition according to claim 9, in the form of a white striped pigmented color gel dentifrice.

17. The composition according to claim 1, wherein the proportion of the deep striped dentifrice component to the base dentifrice component is in the ratio of 60:40% by weight of the white paste dentifrice to the pigmented gel dentifrice.

18. The composition according to claim 1, wherein the proportion of the deep striped dentifrice component to the base dentifrice component is in the ratio of 40:60% by weight of the white paste dentifrice to the pigmented gel dentifrice.

* * * * *